United States Patent [19]

Podhrasky et al.

[11] 4,380,930

[45] Apr. 26, 1983

[54] SYSTEM FOR TRANSMITTING ULTRASONIC ENERGY THROUGH CORE SAMPLES

[75] Inventors: Julius Podhrasky, Dallas; Eve S. Sprunt, Richardson, both of Tex.

[73] Assignee: Mobil Oil Corporation, New York, N.Y.

[21] Appl. No.: 259,773

[22] Filed: May 1, 1981

[51] Int. Cl.³ ............................................. G01N 29/00
[52] U.S. Cl. ...................................... 73/594; 73/571; 367/13
[58] Field of Search ................. 73/571, 594, 599, 618, 73/632; 367/13, 35

[56] References Cited

U.S. PATENT DOCUMENTS 3,537,541 11/1970 Desai et al. ............................ 73/594
4,342,518 8/1982 Shirley ................................. 73/594

*Primary Examiner*—Howard A. Birmiel
*Attorney, Agent, or Firm*—Charles A. Huggett; Michael G. Gilman; George W. Hager

[57] ABSTRACT

A system for measuring ultrasonic (50 Khz–10 Mhz) velocity and attenuation in core samples employs transmitting and receiving transducers for generating and receiving ultrasonic energy in a core sample. The transducer and core sample are contained in a high pressure cell. The transducers are isolated from the high pressure of the cell by suitable housings, allowing the transducers to operate at ambient pressure.

8 Claims, 2 Drawing Figures

SYSTEM FOR TRANSMITTING ULTRASONIC ENERGY THROUGH CORE SAMPLES

BACKGROUND OF THE INVENTION

The theory of wave propagation in elastic materials is well known and has been used for many years in the analysis and synthesis of seismic records. However, real materials in subterranean formations are rarely purely elastic. They are attenuative and dispersive. The attenuation is seen in the change in amplitude of the travelling wave and in the values of the reflection coefficients. The dispersion contributes to the distortion of the recorded seismic events when compared to the clear predictions of the elastic theory. These effects can be compensated if the appropriate values of the velocities and attenuations can be obtained.

Seismic velocity and attenuation depend on many rock properties including minerology, porosity and microstructure. Accordingly it is important to be able to measure velocity and attenuation in core samples taken from the materials of the subterranean formations. A core sample may be positioned between transmitting and receiving transducers and the travel time of ultrasonic (50 khz—10 Mhz) energy through the core sample measured and the waveform recorded for attenuation analysis.

The transmitting transducer is connected to a pulser to generate ultrasonic energy pulses for travel through the core sample. The receiving transducer is connected to an amplifier to increase the received voltage for recording and velocity and attenuation analysis. This is referred to as the "through transmission" technique.

An alternate technique is the "pulse-echo" technique in which a single transducer is utilized alternately in the transmit and receive modes. In this technique the ultrasonic energy pulse travels from the transducer through the core sample until it is reflected from the interface provided by the opposite end of the sample and returns to the sending end of the sample where the transducer, now in the receive mode, detects the returned energy pulse.

SUMMARY OF THE INVENTION

In accordance with the present invention there is provided a system for carrying out ultrasonic velocity measurements and waveform recording in material samples from subterranean formations. Ultrasonic energy means in contact with a material sample transmits ultrasonic energy into the sample and receives energy after it has travelled through the sample. A pressure cell houses the sample and the ultrasonic energy means under a confining pressure. The acoustic energy means is further isolated from such confining pressure by housing means which completely encloses the ultrasonic energy means which is in direct contact with the sample. The housing includes at least one spring-like member for forcing the ultrasonic energy means into direct contact with the sample. Alternatively the energy means may be rigidly fixed within the housing with no provision for relative movement. the housing further includes a passageway through which the fluid pressure within the sample can be selectively adjusted from a suitable fluid pressure supply independently of the confining pressure within the cell.

In one aspect of the invention, the ultrasonic energy means may comprise a first transducer in contact with one end of the sample for transmitting acoustic energy into the sample and a second transducer in contact with an opposite end of the sample for receiving energy after it has traveled through the sample. The two transducers are separately enclosed in suitable housing for isolating the transducers from the confining pressure within the pressure cell.

In an alternate aspect, the ultrasonic energy means may comprise a single transducer in contact with one end of the sample and operating alternately in the transmit and receive modes to transmit ultrasonic energy into the sample and to receive energy upon its reflection from the interface provided by the opposite end of the sample.

DESCRIPTION OF THE PREFERRED EMBODIMENT

Figure 1:
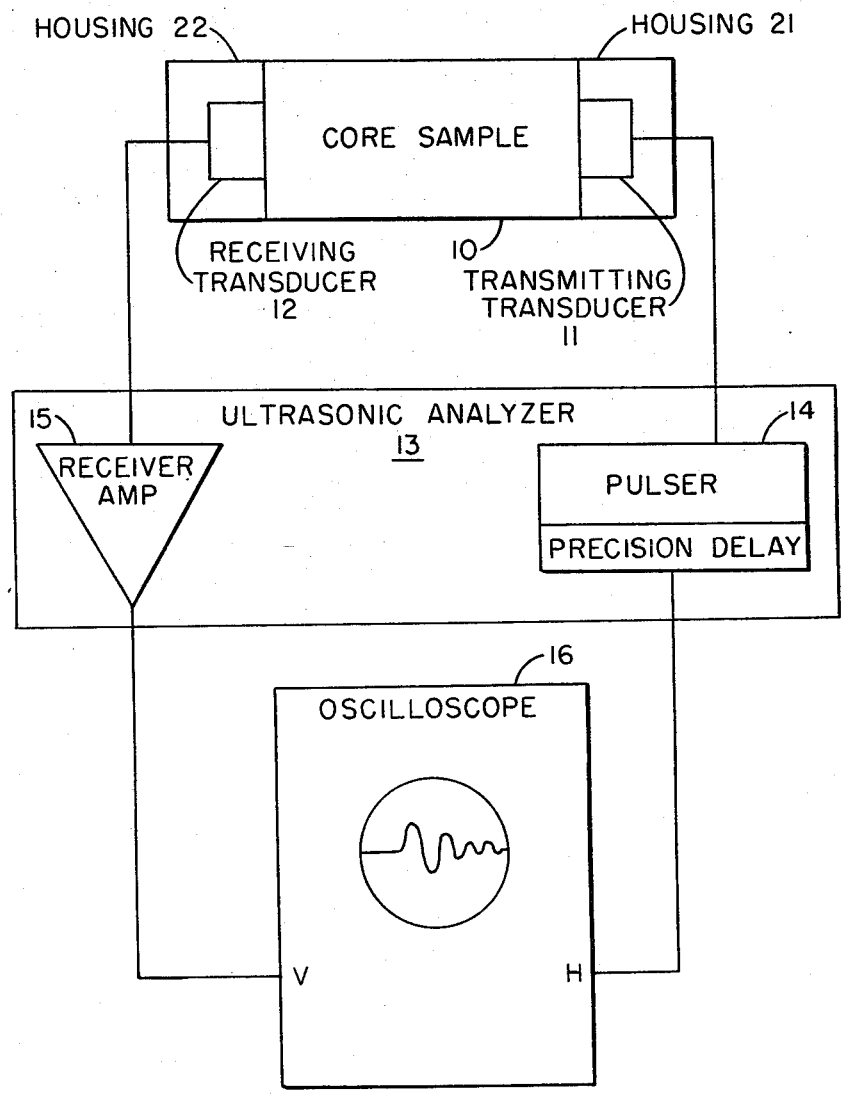
FIG. 1 illustrates a system for measuring ultrasonic velocity and recording waveforms of core samples from subterranean formations.

Referring now to FIG. 1, the core sample 10 from a subterranean formation to be examined in accordance with the present invention is mounted between a transmitting transducer 11 and its housing 11a and a receiving transducer 12 and its housing 12a. These transducers are ultrasonic energy devices such as piezoelectric or magnetostrictive crystals designed to transmit and receive ultrasonic signals. Generation of the ultrasonic signal is carried out by the ultrasonic analyzer 13 including a pulser section 14 and a receiver section 15. The pulser section 14 produces an electrical pulse to excite the transmitting transducer 11, causing it to emit an ultrasonic pulse. This pulse travels through the material of core sample 10 and is converted by the receiving transducer 12 into an electrical signal which is applied to and conditioned by the receiver section 15 of the ultrasonic analyzer 13. This technique is called the "through transmission" technique as the pulse is transmitted by one transducer and received by another. An alternate embodiment might employ the "pulse-echo" technique whereby the pulse travels from the transducer through the material until it is reflected from an interface, such as the other end of the core sample. The reflected pulse may be received by the same transducer and converted into an electrical signal.

In either embodiment, the electrical signal, after being conditioned by the receiver section 15 of the ultrasonic analyzer 13 may be displayed on an oscilloscope 16 for visual interpretation and travel time calculation. The signal may also be recorded by other suitable devices such as a digital waveform recorder 17 or a strip chart recorder 19 for attenuation analysis.

In the embodiment of FIG. 1, the transmitting and receiving transducers 11 and 12 may preferably be Videoscan Contact Transducers as supplied by Panametrics, Inc. of Waltham, Mass. Such transducers are untuned, broadband transducers that provide critically damped, maximum bandwidth performance. They also allow maximum penetration of attenuating or scattering materials, such as core samples of subterranean formations.

The ultrasonic analyzer 13 may be a Panametrics, Inc. Model 5052UA which combines a pulser/receiver in a single unit. The oscilloscope 16 may be a Tektronix 5403 model which provides 60 MHZ bandwidth and a dual time base with suitable time and amplitude expansion for an accurate selection of the acoustic time break.

Figure 2:
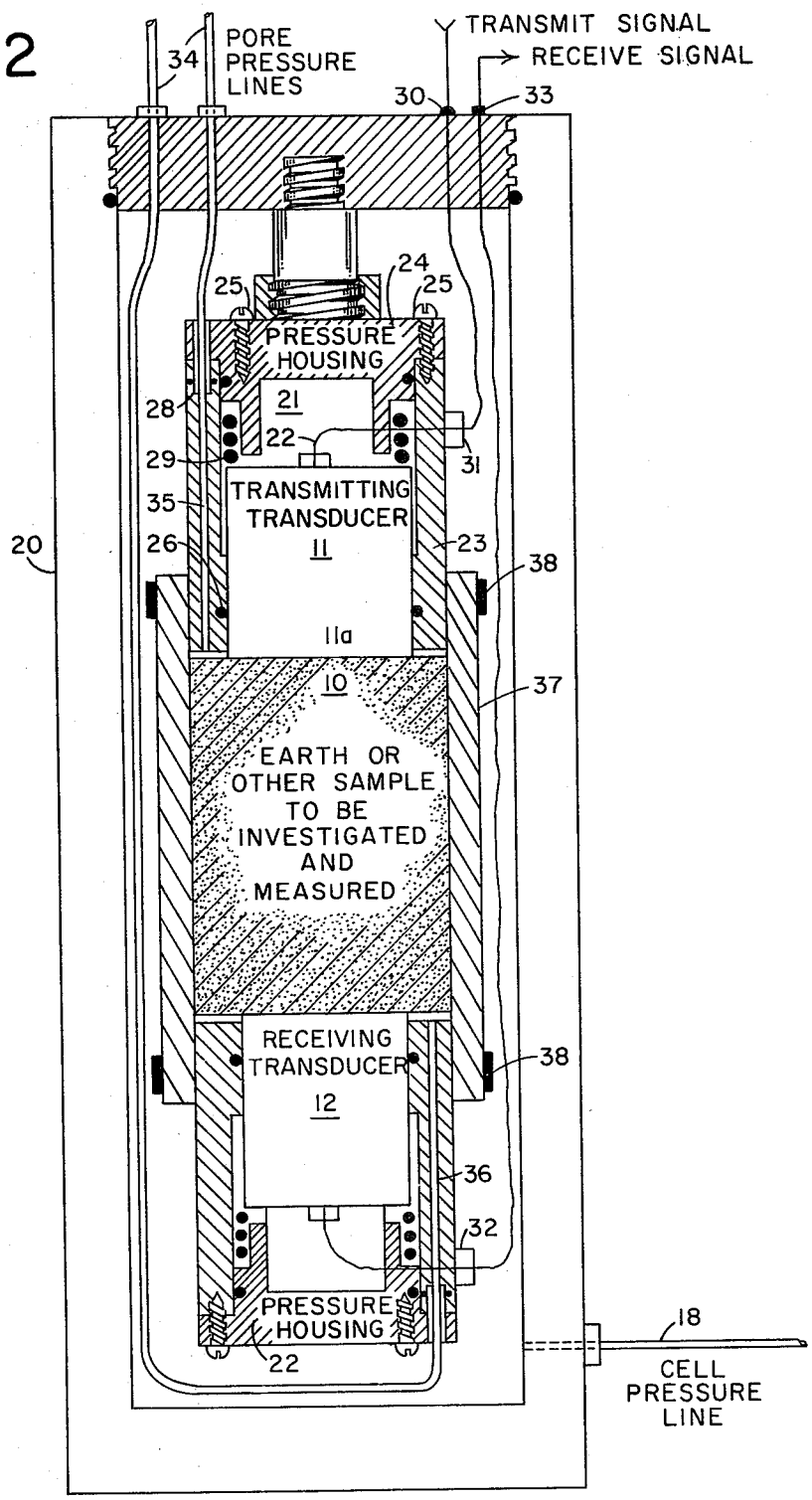
FIG. 2 illustrates the confining pressure cell and transducer housing for use with the ultrasonic velocity and attenuation measuring system of FIG. 1.

Referring now to FIG. 2, there is illustrated a confining pressure cell 20 for use in subjecting the core sample 10 to subterranean pressure conditions and the transducer housings 21 and 22 for isolating the transmitting and receiving transducers, 11 and 12 respectively, from the confining pressure condition within the cell 20 as established by the cell pressure line 18. Core sample 10 is positioned between the transmitting transducer 11 and the receiving transducer 12. Completely enclosing such transducers, except for the faces of the transducers in contact with the core sample 10, are the housings 21 and 22. These housings allow the transducers to operate at ambient or near ambient conditions, thereby permitting the use of conventional ultrasonic transducers which are not designed to operate at the extremely high pressures, up to at least 10,000 pounds per square inch, to which the core sample may be subjected. As both housings 21 and 22 are identical, only housing 21 will be described in further detail.

Housing 21 comprises an annular member 23 having an inside diameter sufficient to be slidably inserted over the transducer 11. A cover member 24 encloses the open end of annular member 23 and is secured by screws 25. O-ring 26 protects the transducer electrical connection 27 from the fluid in the core sample, while O-ring 28 protects the inside of the housing 21, and consequently the transducer 11, from the confining pressure of well 20. The face 11a of transducer 11 is maintained in good contact with the core sample 10 through spring-loading provided by one or more spring-like members 29.

The transmit signal from the pulser section 14 of the ultrasonic analyzer 13 is applied to the transmitting transducer 11 by way of high pressure feed through connectors 30 and 31, while the received signal is applied to the receiver section 15 of the ultrasonic analyzer 13 by way of high pressure feed through connectors 32 and 33.

Pore pressure lines 34 provide the desired fluid pressure to the core sample 10 by way of the passageways 35 and 36 in the housings 21 and 22 respectively.

The core sample 10 and portions of housings 21 and 22 are surrounded by a sleeve 37 which may be made of rubber or other impermeable material. This sleeve is secured by the clamps 38 to further protect the transducers 11 and 12 from the confining pressure within the cell 20.

The foregoing has described an ultrasonic velocity and attenuation measuring system employing the ultrasonic energy means housing of the present invention. It is to be understood that various modifications to the disclosed embodiment may become apparent to one skilled in the art without departing from the scope and spirit of the invention as hereinafter defined by the appended claims.

What is claimed is:

1. A system for transmitting ultrasonic energy through a material sample comprising:
   (a) ultrasonic energy transducing means in contact with said material sample for transmitting ultrasonic energy into said sample and for receiving the energy after it has traveled through said sample,
   (b) a pressure cell for housing said sample under a confining pressure simulating subterranean pressure conditions, and
   (c) means for isolating said ultrasonic energy transducing means from the confining pressure condition on said cell such that said ultrasonic energy transducing means operates at ambient pressure conditions.

2. The system of claim 1 wherein said means for isolating said ultrasonic energy transducing means from said confining pressure comprises a housing adapted for completely enclosing said ultrasonic energy transducing means excepting only for the face of said ultrasonic energy transducing means which is in direct contact with said sample.

3. The system of claim 2 wherein said ultrasonic energy transducing means is slidably mounted within said housing, said housing is spaced apart from said sample, and said housing includes at least one spring-like member for forcing said ultrasonic energy transducing means into contact with said sample.

4. The system of claim 2 wherein said housing includes a passageway through which the fluid pressure within the sample can be selectively adjusted from a suitable fluid pressure supply independently of the confining pressure within said cell.

5. The system of claim 1 wherein said ultrasonic energy transducing means operates at ambient pressure within said housing while the sample is under a confining pressure up to 10,000 pounds per square inch.

6. The system of claim 1 wherein said ultrasonic energy transducing means operates alternately in the transmit and receive modes to transmit ultrasonic energy into said sample and to receive the energy upon its reflection from the interface provided by the opposite end of the sample.

7. The system of claim 1 wherein said ultrasonic energy transducing means comprises:
   (a) a first transducer in contact with a first end of said sample for transmitting ultrasonic energy into said sample,
   (b) a second transducer in contact with a second end of said sample for receiving energy after it has travelled through said sample.

8. The system of claim 7 wherein said isolating means comprises:
   (a) a first housing adapted for completely enclosing said first transducer excepting only for the face of said first transducer which is in contact with said first end of said sample, and
   (b) a second housing adapted for completely enclosing said second transducer excepting only for the face of said second transducer which is in contact with said second end of said sample.

* * * * *